(12) United States Patent
Thiem

(10) Patent No.: US 8,042,444 B2  
(45) Date of Patent: Oct. 25, 2011

(54) KNIFE HOLDER FOR MICROTOME BLADES

(75) Inventor: Stefan Thiem, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 87 days.

(21) Appl. No.: 11/577,726

(22) PCT Filed: Oct. 15, 2005

(86) PCT No.: PCT/DE2005/001840  
§ 371 (c)(1),  
(2), (4) Date: May 20, 2009

(87) PCT Pub. No.: WO2006/045270  
PCT Pub. Date: May 4, 2006

(65) Prior Publication Data  
US 2009/0235799 A1  Sep. 24, 2009

(30) Foreign Application Priority Data  
Oct. 25, 2004 (DE) .......... 10 2004 051 974

(51) Int. Cl.  
*B26D 7/26* (2006.01)  
*G01N 1/06* (2006.01)

(52) U.S. Cl. .......... 83/856; 83/425; 83/698.11; 83/703; 83/915.5; 83/954; 83/DIG. 1

(58) Field of Classification Search .......... 83/915.5, 83/954, 425, 435.11, 437.1, 544–546, 698.11, 83/703, 713, 856, DIG. 1; 30/346.5, 346.52–346.55, 346.58, 346.59, 346.6, 346.61; 483/60–62  
See application file for complete search history.

(56) References Cited

U.S. PATENT DOCUMENTS

| | | | | |
|---|---|---|---|---|
| 1,005,193 A * | 10/1911 | Gates | ............... | 30/50 |
| 1,877,149 A * | 9/1932 | Sylvan | ............... | 30/346.57 |
| 2,059,172 A * | 10/1936 | Sabiers | ............... | 30/527 |
| 2,125,502 A * | 8/1938 | Holtzman | ............... | 30/346.61 |
| 2,653,379 A * | 9/1953 | Austin | ............... | 30/40.2 |
| 4,114,780 A * | 9/1978 | Sharon | ............... | 221/101 |
| 4,207,790 A | 6/1980 | Endo | | |
| 4,534,110 A * | 8/1985 | Glass | ............... | 30/346.57 |
| 5,669,278 A | 9/1997 | Metzner | | |
| 5,964,138 A | 10/1999 | Metzner et al. | | |
| 7,146,894 B2 * | 12/2006 | Hendrick et al. | ............... | 83/703 |
| 7,166,117 B2 * | 1/2007 | Hellenkamp | ............... | 606/166 |
| 2001/0003938 A1 | 6/2001 | Heid | | |
| 2002/0005104 A1 | 1/2002 | Hendrick et al. | | |
| 2004/0194604 A1 * | 10/2004 | Fischer | ............... | 83/651 |
| 2005/0115373 A1 * | 6/2005 | Kunkel | ............... | 83/168 |

FOREIGN PATENT DOCUMENTS  
GB  2238973 A  6/1991

\* cited by examiner

*Primary Examiner* — Clark F. Dexter  
(74) *Attorney, Agent, or Firm* — Hodgson Russ LLP (57) ABSTRACT

A knife holder (1) for microtome blades (2) has a body (3) for reception of the blade (2) against an abutment edge (4) and a pressure plate (5) for retention of the blade, such that in the retained state, only the blade cutting edge (6) protrudes from the body (3), and an ejection apparatus (8), associated with one side edge (7) of the blade cutting edge (6), is connected to the body (3).

9 Claims, 8 Drawing Sheets

KNIFE HOLDER FOR MICROTOME BLADES

CROSS-REFERENCE TO RELATED APPLICATIONS

The present application is the U.S. National Stage of International Application No. PCT/DE2005/001840 filed Oct. 15, 2005, which claims priority of German Application No. 10 2004 051 974.9 filed Oct. 25, 2004.

FIELD OF THE INVENTION

The present invention relates to a knife holder for microtome blades, the knife holder being of a type having a body including an abutment surface, and a pressure plate connected to the body and adjustable relative to the body for clamping a microtome blade received against the abutment surface.

BACKGROUND OF THE INVENTION

Microtomes serve to produce thin sections of various samples in the fields of medicine, biology, and botany, materials research, and quality control of engineering materials. These thin sections are produced with knives of different configurations and types. Steel knives made of selected tool steels, manufactured with various types of edge grinding, are known. In addition to these solid regrindable knives, blade-like cutting knives (so-called disposable blades) are widely used. Disposable blades are usually replaced by new ones once their service life has been exceeded. In addition, glass knives and diamond knives are in use for specific applications.

For all types of knife, a plurality of knife carriers and knife holders are known in microtome technology; these additionally differ, in terms of their configuration, depending on the type of microtome for which they are provided. The knife holders that are used perform the principal function of retaining the particular microtome blade in stable fashion in order to achieve the desired sectioning result.

A knife holder having a pressure plate for retaining a blade-like cutting knife is known from DE 44 35 072 C1. The knife holder contains a body and a retaining jaw having an abutment edge on which the back side of the cutting knife rests. The cutting knife is pressed, with the pressure plate, against the retaining jaw. The length of the abutment edge can be greater than the length of the cutting knife. By appropriate positioning of the cutting knife along the abutment edge, a respectively sharper region of the blade cutting edge can be associated with the specimen to be sectioned.

A knife holder for a solid regrindable wedge-shaped steel knife is depicted and described in DE 195 06 837 C1. The steel knife of itself generally exhibits sufficient stability that it is usually retained only in its end regions.

In addition to a stable retaining system that is intended to prevent vibrations at the knife, most knife holders possess devices for setting the relief angle between the knife cutting edge and sample. A device of this kind can be made up, for example, of a circular-segment curved member mounted pivotably on a base, on which member the body of the knife holder is secured. When a user is working with microtomes, the risk always exists of cutting injuries to his or her hand because the blade cutting edge of the microtome knife protrudes from the knife holder. Especially in the context of sample changes, the operator must manually exchange, in the vicinity of the microtome knife, sample cassettes that are located in a clamping system. To avoid injuries, the blade length selected is preferably so short that it does not project laterally from the body. In the retained state, only the blade edge protrudes out of the body. In addition, knife holders can comprise a so-called finger protector. A finger protector of this kind can be made up of a rectangular frame, articulated pivotably on the body of the knife holder, whose bridge joining the two limbs of the U extends, in one end position, over the blade cutting edge and thereby prevents inadvertent contact against the blade cutting edge. A finger protector of this kind may be inferred, for example, from DE 198 24 024 A1.

The risk of injury to the operator is greatest, however, when the maximum service life of the cutting knives has been reached, i.e. they no longer have the sharpness necessary for thin sections and must be replaced. For this, the finger protector must be swung back, the pressure plate must be released, and the microtome blade must be pushed laterally out of the knife holder, using an aid such as a brush handle or the like, until the blade can be grasped with the fingers. To simplify this cumbersome procedure while avoiding the need for assistance from additional aids, in known knife holders the blade length was often selected, specifically in the case where disposable blades were used, so that in the retained state it protrudes to the left and right, but at least on one side, beyond the width of the body with its pressure plate, so as thereby to be more easily graspable. A disadvantage here is that because stable retention is lacking, the microtome knife is not usable in the projecting peripheral region, and this simultaneously constitutes an additional source of risk during the cutting operation and when samples are changed.

SUMMARY OF THE INVENTION

It is therefore the object of the present invention to make available a knife holder for microtome blades in which on the one hand the risk of injury is reduced as much as possible, and on the other hand worn-out microtome blades can easily be brought, without additional separate aids, into a position in which they are easily graspable outside the blade cutting edge.

This object is achieved according to the present invention, in the context of a knife holder of the kind cited initially, in that an ejection apparatus, associated with one side edge of the blade cutting edge, is connected to the body. Advantageous refinements of the knife holder according to the present invention are the subject matter of the dependent claims.

The ejection apparatus is equipped for this purpose with an ejection element acting on the blade cutting edge. As long as the ejection apparatus is not actuated by the operator, a spring element holds the ejection element in the idle position outside the side edge. A configuration of the ejection apparatus as a lever mechanism, having a flat ejection lever whose thickness is adapted to the blade thickness, is advantageous. The flat ejection lever can thus be brought, as soon as the pressure plate is released, into working engagement against one of the side edges of the blade. Assuming that complete ejection of the microtome blade is acceptable, it is also possible, in the context of a corresponding configuration of the body, for the ejection lever to act on the lower edge of the microtome blade.

In a further embodiment of the invention, the ejection apparatus contains a plunger mechanism whose plunger head is directed onto a side edge of a protruding cutting edge portion of the blade. A "side edge of a protruding cutting edge portion of the blade" is understood as the region of the microtome blade that, in the retained state, protrudes freely out of the knife holder adjacently to the blade cutting edge. Upon actuation of the plunger mechanism, a motion tangential to the abutment edge of the microtome blade is imparted to a generally pin-shaped plunger, the plunger head is brought into working engagement with the side edge of the protruding cutting edge portion of the blade, and the microtome blade is thus ejected laterally. Because of the orientation of the plunger head with respect to the side edge of the protruding cutting edge portion of the blade, the plunger head can be dimensioned with a larger area. This facilitates alignment of the ejection apparatus.

It is particularly advantageous in this connection to provide, as the actuation element of the plunger mechanism, a pushbutton that is under a spring load and is rigidly joined to the plunger. The spring load can be generated by a variety of spring elements. A helical spring wound around the plunger offers particular advantages in terms of compactness and maximum displacement travel of the plunger mechanism. The ejection apparatus can of course be fixedly joined to the body at any region of the knife holder, provided the microtome blade can be brought, by the actuation of said apparatus, into a position in which it can be securely grasped by the operator.

Further advantages are offered by an arrangement according to the present invention in which a rectangular frame that is pivotable via the pressure plate is connected to the body in such a way that in an end position above the blade cutting edge, the frame's bridge rests on the pressure plate, the ejection apparatus being arranged on the frame in the region of the bridge. The frame can be embodied in such a way that when sections are being produced, its bridge covers the blade cutting edge in such a way that contact therewith is effectively prevented, and said frame thus functions as a finger protector. As soon as the pressure plate is released, a used microtome blade can be ejected laterally from the knife holder by actuation of the ejection apparatus, without exposing the operator to the risk of contacting the blade cutting edge. As soon as the microtome blade has been laterally ejected far enough, it can be grasped for blade-changing purposes and removed. If the blade should not have been ejected far enough beneath the frame, the frame can be swung back; this on the one hand simplifies lateral removal of the used blade, and on the other hand additionally and advantageously exposes the knife holder for introduction of a new microtome blade.

BRIEF DESCRIPTION OF THE DRAWINGS

An exemplifying embodiment of the knife holder according to the present invention is depicted schematically in the drawings and will be described in further detail below with reference to the Figures, further advantages being presented. In the drawings.

DETAILED DESCRIPTION OF THE INVENTION

Figure 1:
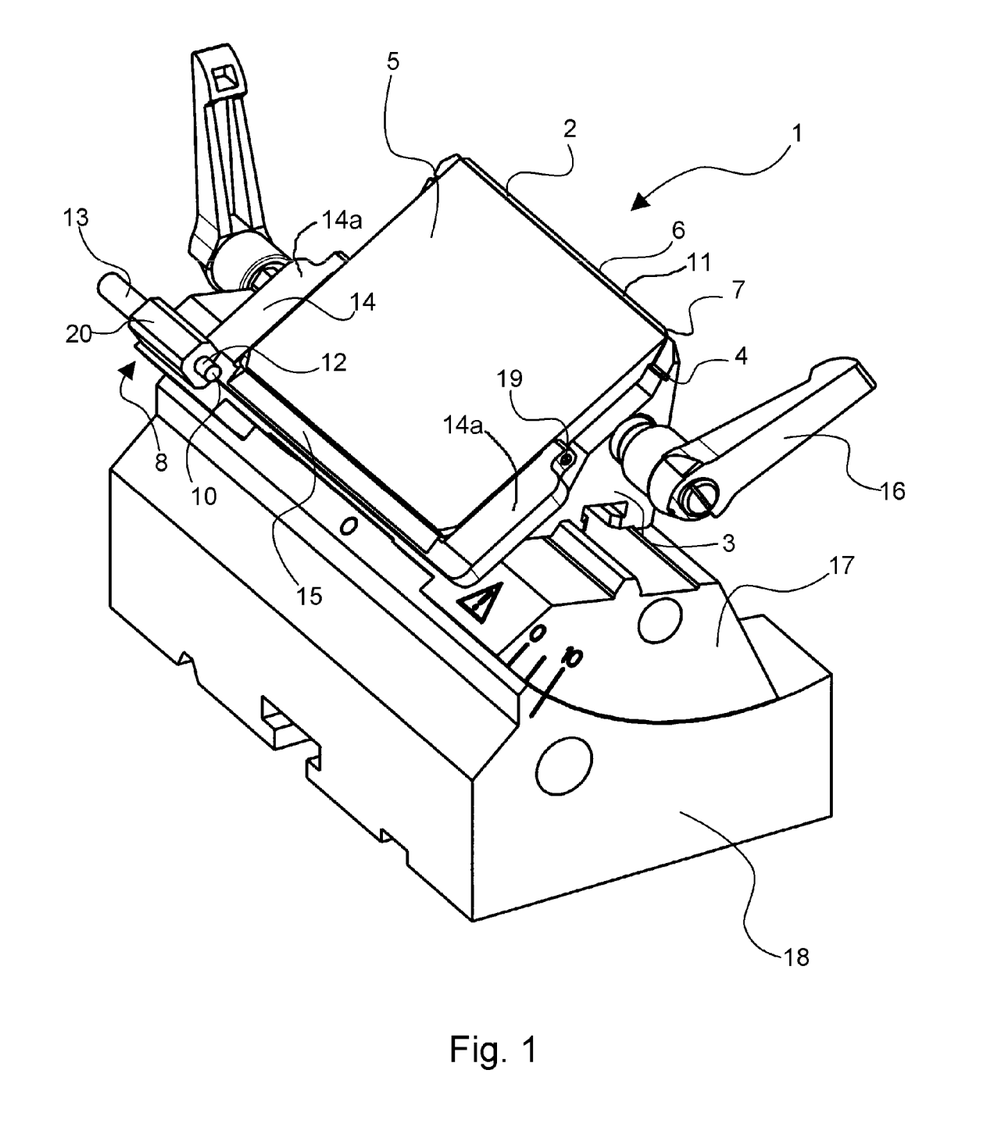
FIG. 1 shows a knife holder with a frame swung downward.

FIG. 1 is a view of a knife holder 1 according to the present invention in which a microtome blade 2 abuts against an abutment edge 4 and is clamped in between body 3 and pressure plate 5 with the aid of a clamping toggle 16. The length of microtome blade 2 is selected to be sufficiently short that it is retained over its entire length and is thus completely usable. Only blade cutting edge 6 protrudes out of knife holder 1. In order to make blade cutting edge 6 usable over its entire length, body 3 is laterally displaceable on a segmental curved member 17 parallel to blade cutting edge 6. Segmental curved member 17 is mounted, in known fashion, pivotably along its cylindrical rear surface on a base 18, so that the so-called relief angle, i.e. the orientation of microtome blade 2 relative to the specimen (not depicted further) to be sectioned, is adjustable.

Articulated on pressure plate 5 is a rectangular frame 14 that is pivotable about a pivot axis 19 and is in a swung-back position. An ejection apparatus 8 is mounted on one side of bridge 15 that connects the two limbs 14a, 14a of the U. Ejection apparatus 8 is made up of a guide 20 in which pushbutton 13, joined rigidly to an ejection element in the form of a plunger 12, is movably mounted. The axis of plunger 12 proceeds parallel to abutment edge 4.

Figure 2:
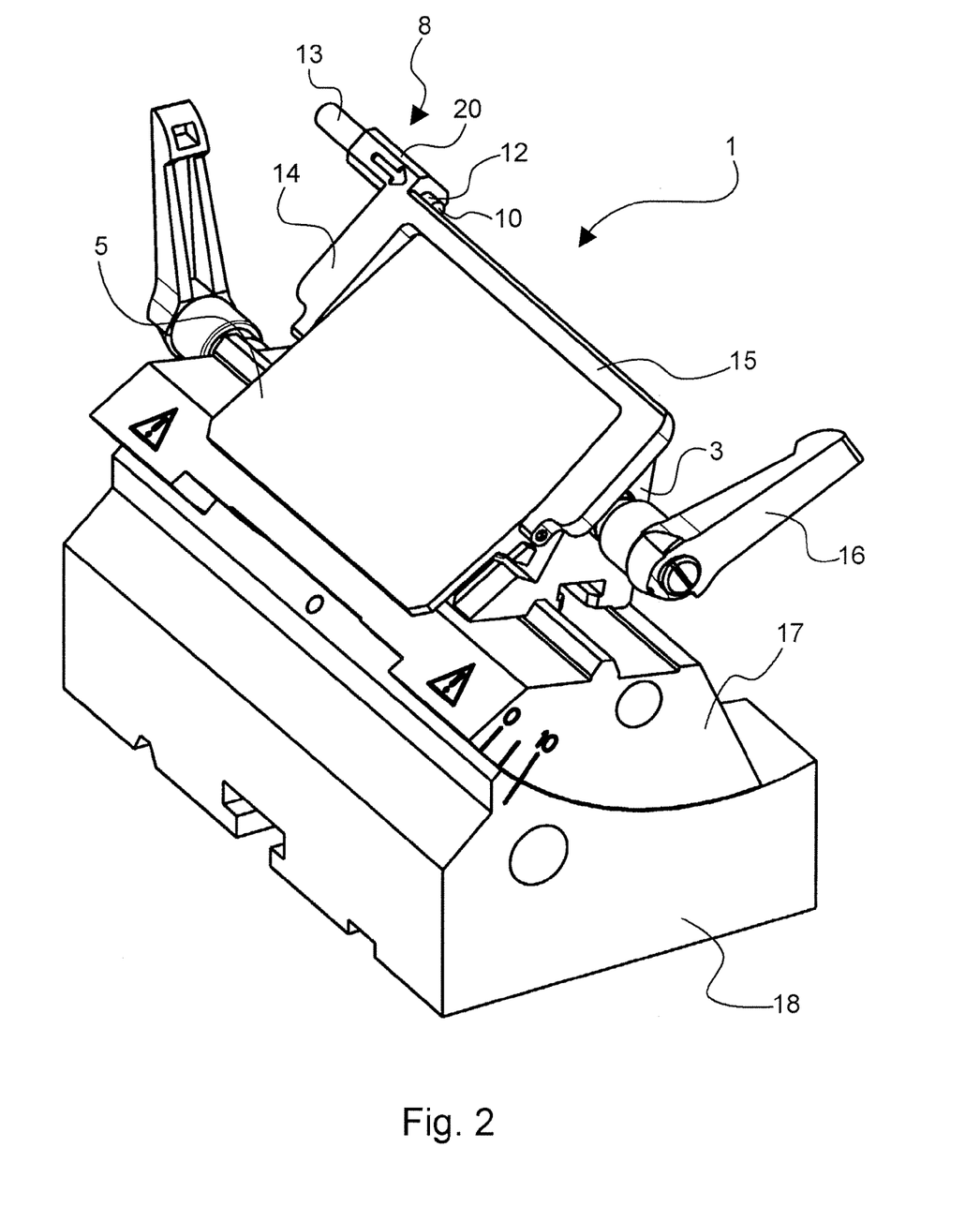
FIG. 2 shows the knife holder with a frame swung upward.

FIG. 2 shows knife holder 1 with the frame 14 swung upward. In this end position, bridge 15 extends over microtome blade 2 (not visible in this depiction) and thus prevents inadvertent contact with the otherwise exposed blade cutting edge 6. As a result of inward pressure on pushbutton 13 which is under spring load, plunger 12 is displaced in the direction of microtome blade 2, plunger head 10 is brought into working engagement with microtome blade 2, and the latter is ejected by further inward pressure.

Figure 3:
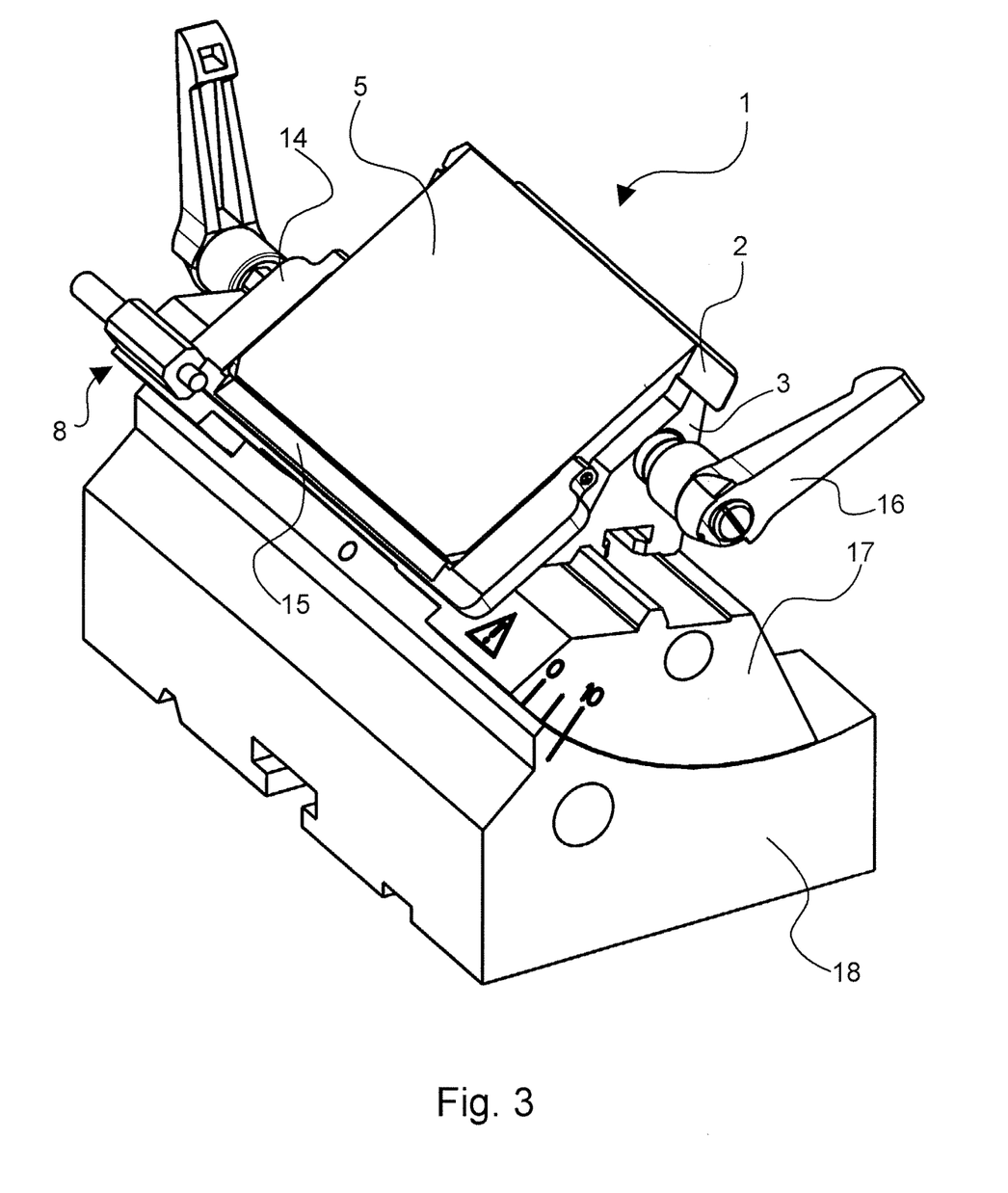
FIG. 3 shows a microtome blade pushed out laterally.

In FIG. 3, microtome blade 2 is illustrated in an ejected position. It protrudes laterally beyond body 3 sufficiently far that it can easily be grasped by the operator for complete removal. Frame 14 is once again in the same position as depicted in FIG. 1.

Figure 4:
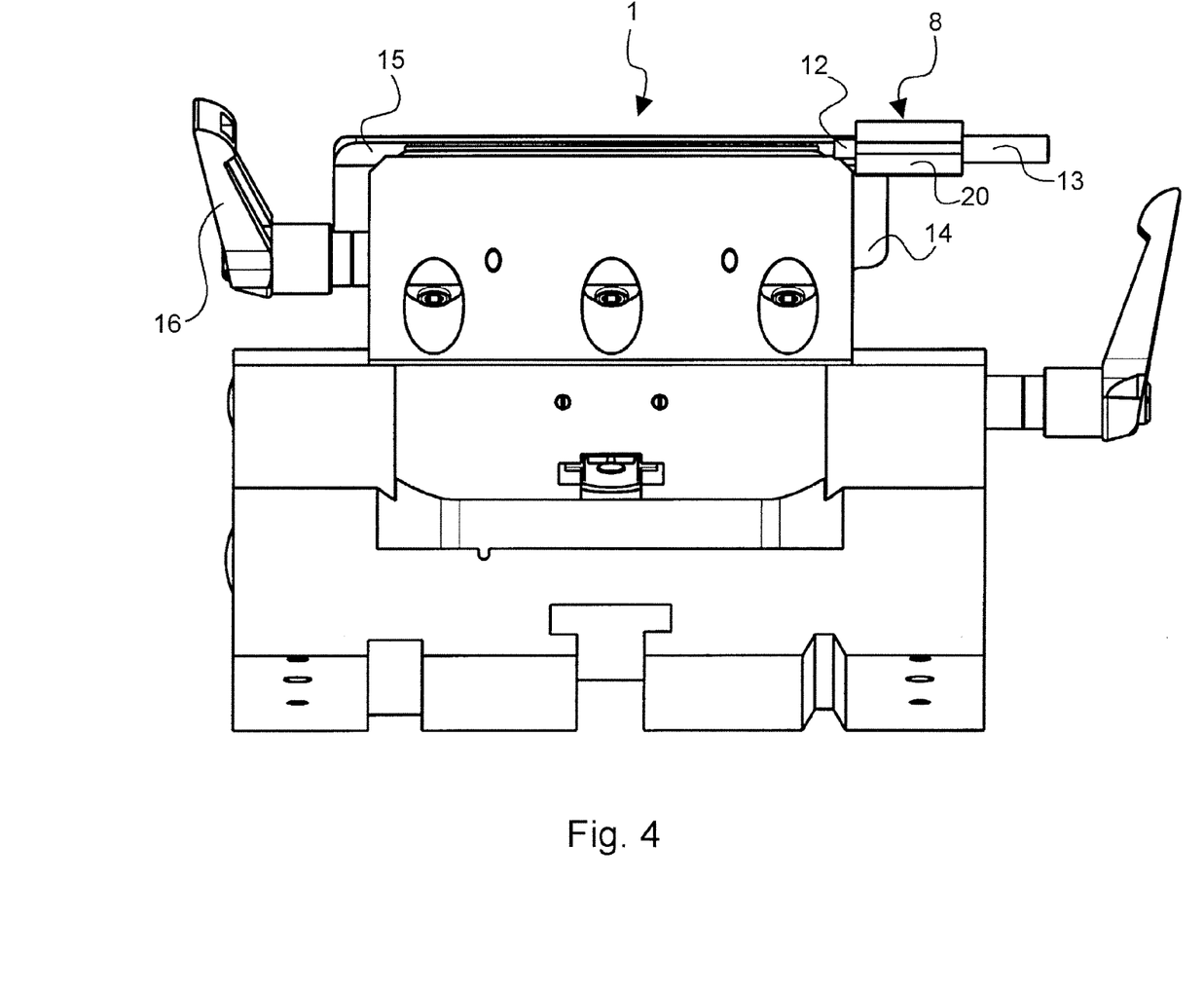
FIG. 4 is a rear view of the knife holder, with the ejection apparatus in the idle position.

The rear view of knife holder 1 depicted in FIG. 4 shows frame 14 swung upward, with ejection apparatus 8 mounted thereon in the idle position as in FIG. 2. Pushbutton 13 and plunger 12 constitute an axis that proceeds through guide 20.

Figure 4A:
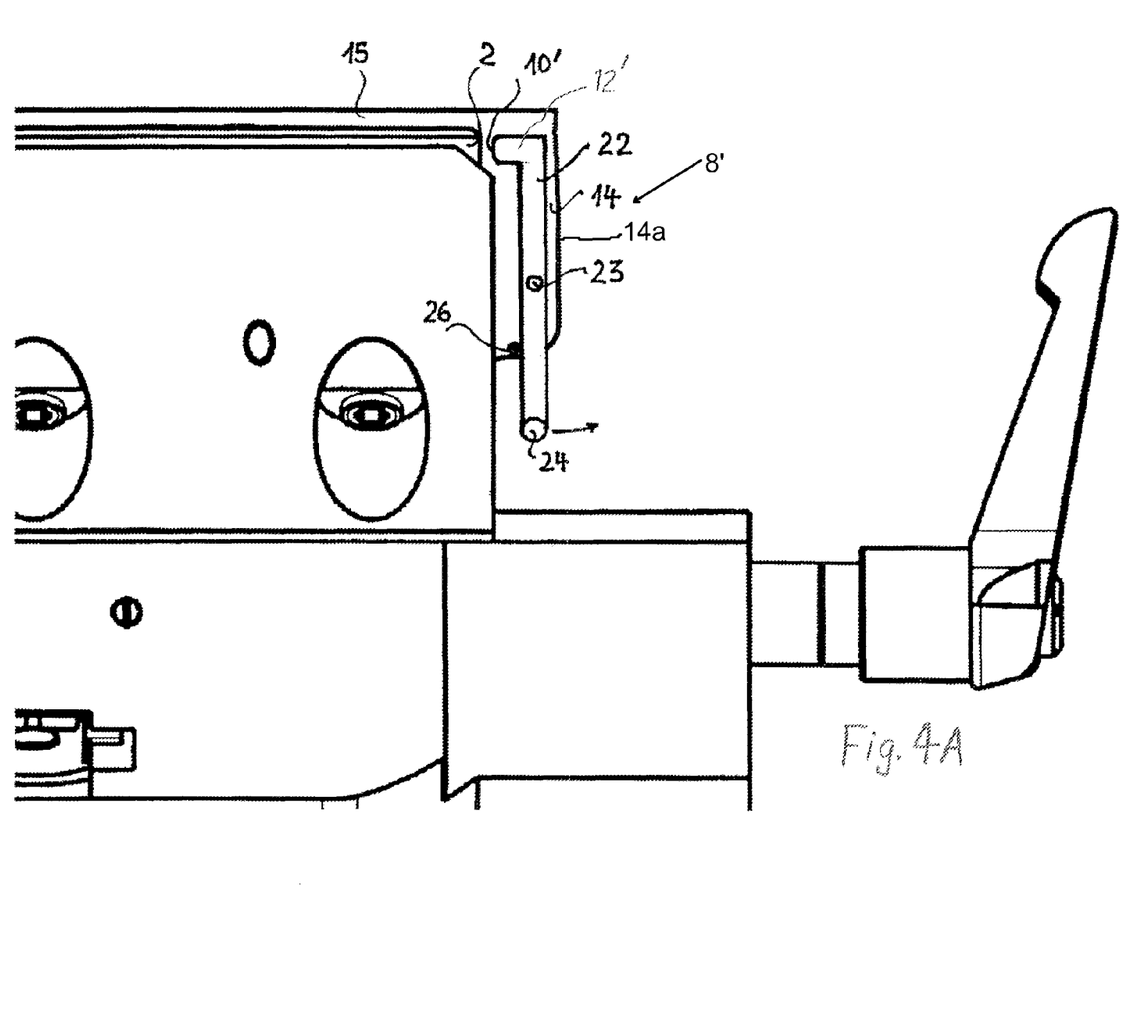
FIG. 4A is a partial rear view of the knife holder, showing an ejection apparatus formed in accordance with an alternative embodiment of the invention, in the idle position.

FIG. 4A shows knife holder 1 having an ejection apparatus 8' formed according to an alternative embodiment wherein an ejection element, plunger 12', is carried by a lever 22 and includes a plunger head 10' for engaging a side edge of the protruding cutting edge portion of blade 2. Lever 22 is pivotally mounted on a leg or limb 14a of frame 14 by a pivot pin 23, and a detent pin 26 is arranged on the leg of frame 14 to limit pivotal movement of the lever. Lever 22 further includes a knob 24 at an end opposite the plunger 12'. As may be understood, lever 22 can be pivoted in a counter-clockwise direction as shown in FIG. 4A to cause plunger head 10' to engage blade 2. A spring element, not visible, may be provided to bias lever 22 in a clockwise direction to maintain plunger 12' in an idle position away from contact with the blade when the ejection apparatus 8' is not in use. For example, a torsion spring at pivot pin 23, or a compression or extension spring between lever 22 and frame 14, may be used.

Figure 5:
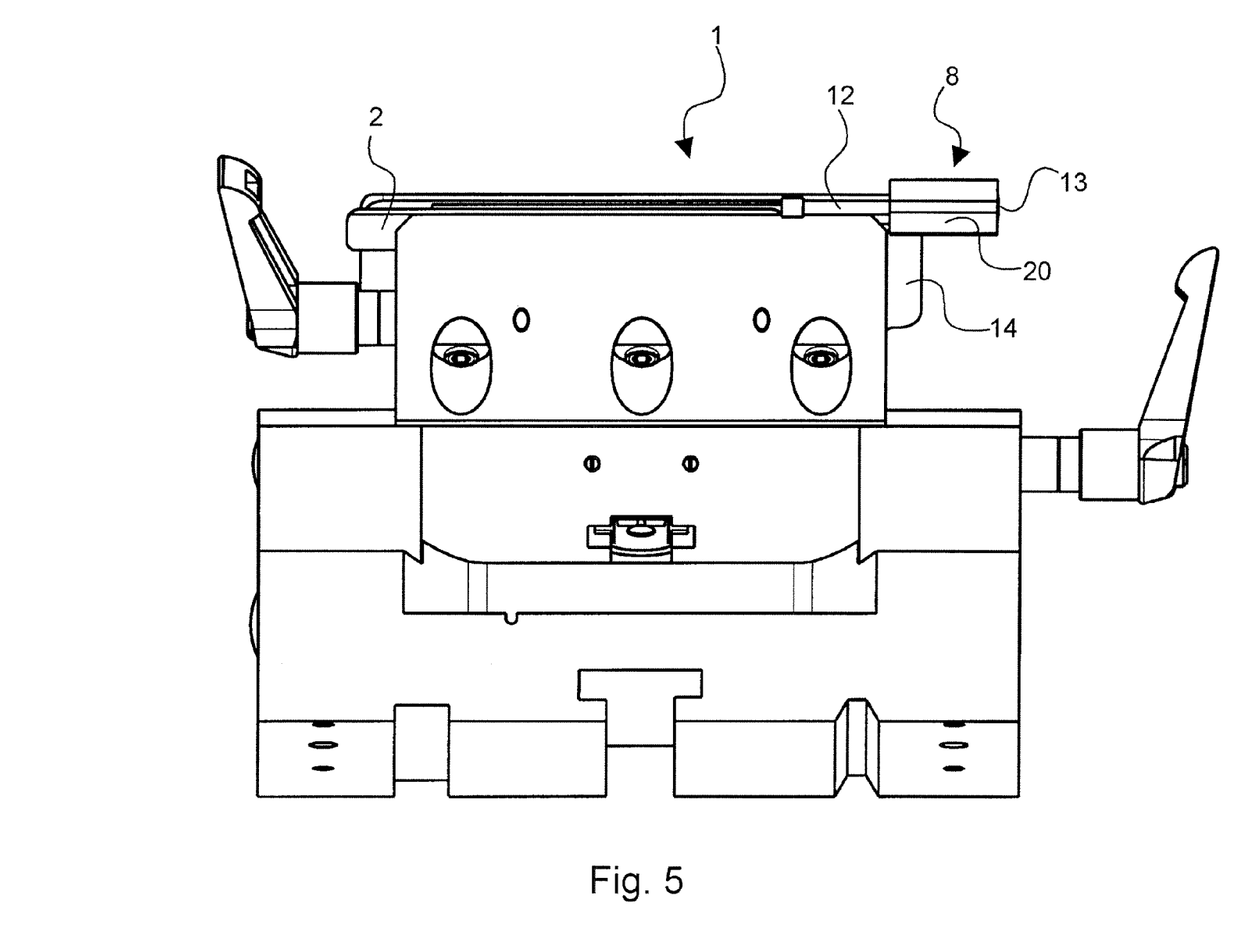
FIG. 5 shows an ejection apparatus in the pushed-in state.

FIG. 5 shows knife holder 1 in a further rear view; pushbutton 13 is pushed completely into guide 20 and plunger 12 therefore protrudes well out of the guide 20. Microtome blade 2 is in an ejected position.

Figure 6:
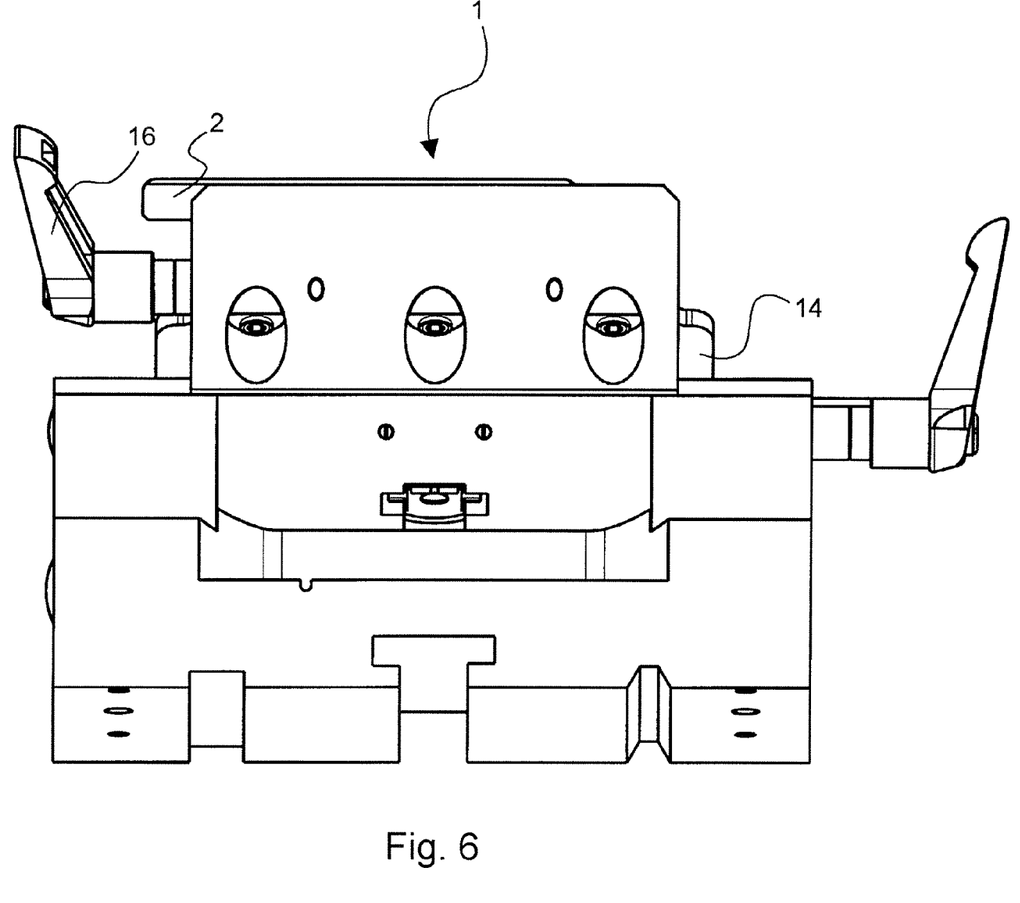
FIG. 6 is a rear view of the knife holder as in FIG. 3.

FIG. 6 depicts knife holder 1 with an ejected microtome blade 2. Pivotable frame 14 is in a swung-down position and thus exposes the laterally ejected microtome blade 2 to be grasped by the operator.

Figure 7:
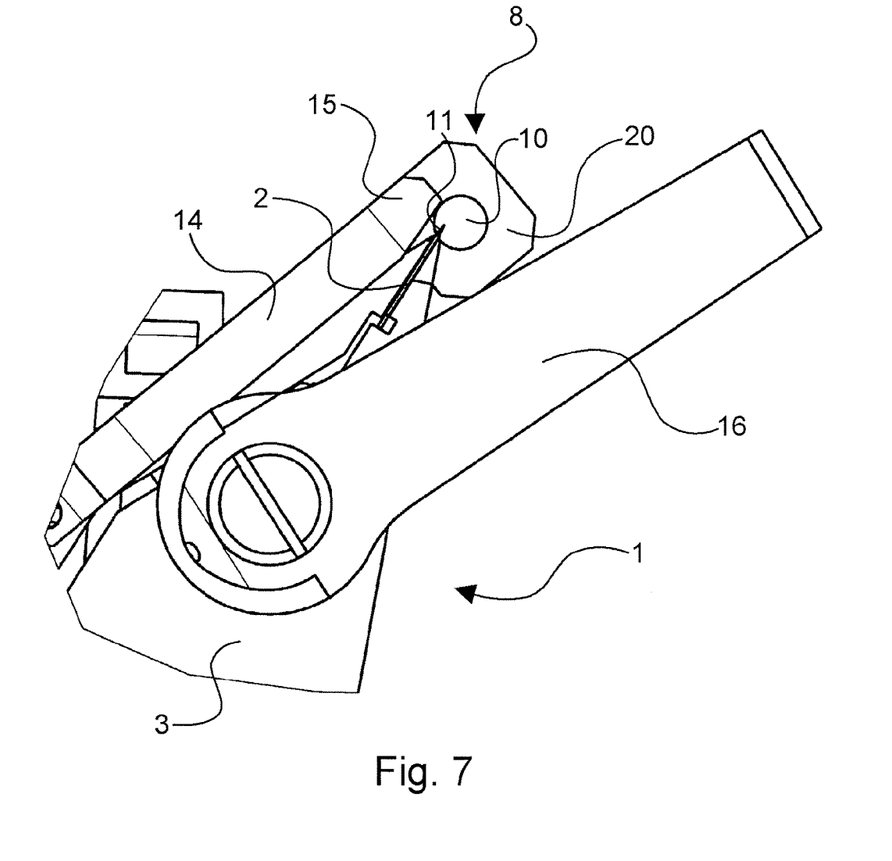
FIG. 7 shows a detail of a lateral view of the knife holder.

FIG. 7 shows an enlarged side detail of knife holder 1 looking perpendicularly at plunger head 10. The end surface of plunger head 10 is associated with a side edge 7 (FIG. 1) of a protruding cutting edge portion 11 of microtome blade 2. Guide 20, mounted on frame 14 in the region of bridge 15, is clearly visible in the enlarged view.

Figure 8:
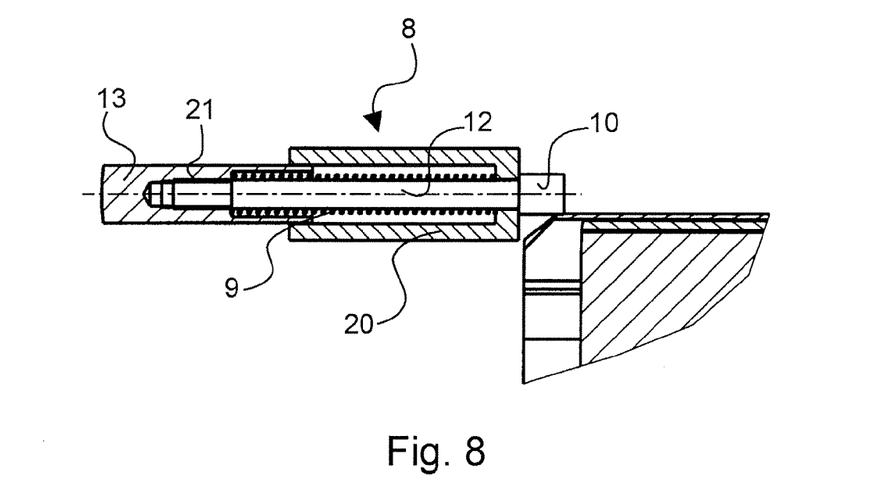
FIG. 8 shows a section through the ejection apparatus.

FIG. 8 depicts ejection apparatus 8 in section. Pushbutton 13 is rigidly joined to plunger 12 via a threaded connection 21. In guide 20, a spring element 9 generates a preload that holds the plunger head 10, in the idle position, in abutment against guide 20.

PARTS LIST

1 Knife holder
2 Microtome blade
3 Body
4 Abutment edge
5 Pressure plate
6 Blade cutting edge
7 Side edge
8, 8' Ejection apparatus
9 Spring element
10, 10' Plunger head
11 Protruding cutting edge portion of blade 2
12, 12' Plunger
13 Pushbutton
14 Frame
14a Limb
15 Bridge
16 Clamping toggle
17 Segmental curved member
18 Base
19 Pivot axis
20 Guide
21 Threaded connection
22 Lever
23 Pivot pin
24 Knob
26 Detent pin

What is claimed is:

1. A knife holder for a microtome blade comprising:
a body including an abutment edge for abutting a microtome blade;
a pressure plate connected to the body and adjustable relative to the body for mounting the microtome blade therebetween;
a frame including at least one limb and an elongated bridge extending from the at least one limb parallel to the abutment edge, the frame being pivotally mounted for rotation about a pivot axis extending parallel to the abutment edge, wherein the frame pivots between a first position wherein the bridge is proximate the abutment edge and a second position wherein the bridge is distal from the abutment edge; and
an ejection apparatus attached to and pivotable with the frame, the ejection apparatus including an ejection element carried by the frame and movable relative to the frame in a blade ejecting direction while the frame is stationary in the first position for ejecting the microtome blade.

2. The knife holder according to claim 1, wherein the ejection apparatus includes a spring element arranged to bias the ejection element in a direction opposite from the blade ejecting direction.

3. The knife holder according to claim 1, wherein the ejection apparatus includes an ejection lever to which the ejection element is fixed, wherein the ejection lever is pivotally mounted on one of the limbs of the frame at a location spaced from the ejection element, wherein the ejection element is movable by pivoting the ejection lever.

4. The knife holder according to claim 3, wherein the ejection lever is flat with a thickness adapted to the blade thickness so that, upon a release of the pressure plate, the lever can be brought into working engagement with one of the side edges of the microtome blade.

5. The knife holder according to claim 1, wherein the ejection apparatus includes a guide in which the ejection element is slidably received.

6. The knife holder according to claim 5, wherein the ejection element is guided for linearly directed movement by the guide.

7. The knife holder according to claim 5, wherein the ejection apparatus includes a pushbutton fixed to the ejection element.

8. The knife holder according to claim 7, wherein a spring element is arranged to act between the pushbutton and the guide.

9. The knife holder according to claim 1, wherein the frame is U-shaped and the at least one limb comprises a pair of limbs connected to one another by the bridge.

* * * * *